United States Patent [19]

Monthony et al.

[11] 3,948,743

[45] Apr. 6, 1976

[54] METHOD FOR GEL ELECTROPHORESIS

[75] Inventors: James F. Monthony, Albany; Christopher J. Siebert, Berkeley, both of Calif.

[73] Assignee: Bio-Rad Laboratories, Richmond, Calif.

[22] Filed: Apr. 14, 1975

[21] Appl. No.: 567,672

[52] U.S. Cl. .................. 204/180 G; 204/299 R
[51] Int. Cl.² .................................. B01K 5/00
[58] Field of Search ....... 204/180 G, 299; 23/253 R, 23/253 TP, 111

[56] References Cited
UNITED STATES PATENTS

| | | | |
|---|---|---|---|
| 2,976,576 | 3/1961 | Wichterle et al. | 204/180 G X |
| 3,384,564 | 5/1968 | Ornstein et al. | 204/180 G |
| 3,494,846 | 2/1970 | Arquembourg | 204/180 G |
| 3,527,712 | 9/1970 | Renn et al. | 204/180 G X |

*Primary Examiner*—T. Tung
*Assistant Examiner*—A. C. Prescott
*Attorney, Agent, or Firm*—Townsend and Townsend

[57] ABSTRACT

Gels for electrophoresis such as polyacrylamide gels are formed in a neutral pH medium containing a salt solution of preselected concentration. This salt is incorporated in the gel and in subsequent use in electrophoresis is displaced upon application of an electrical potential (direct current) by ionic species which form a pH buffer in the gel. Prior to introduction of the buffer, the gel containing the neutral salt is storage stable for prolonged periods of time. The gel is reproducible since it is always formed under the same conditions and the buffer only thereafter introduced.

14 Claims, No Drawings

METHOD FOR GEL ELECTROPHORESIS

This invention relates to gel electrophoresis. More particularly it relates to a novel gel formed in a neutral salt solution and the use of such a gel by electrophoretically introducing a buffer.

Electrophoresis exploits differences in mass to charge ratios and/or molecular size to separate molecules. Originally, the technique was carried out by placing a zone of unresolved components in aqueous buffered solution within a carefully designed electrophoresis cell. A direct current potential was applied to the device and the relative movement of components observed. Thermal convection severely limited the technique. The introduction of porous media such as cellulose acetate, paper or agar stabilized the solution, greatly improving the practical use of electrophoresis. Such media are now widely used and are commercially available in ready-to-use forms. A person requires minimal specialized skills to achieve good results. The introduction of polyacrylamide gel electrophoresis provided not only zone stabilization but also the convenient control of gel pore size. (Ornstein, L., Ann. New York Acad. Sci. 121, 321 (1964), and Davis, B. J., ibid, 121,404 (1964). Separations based primarily on size of the components became readily possible. Polyacrylamide gel electrophoresis is now widely used and is generally regarded as one of the most sensitive techniques available for resolving subtle mixtures of components in certain molecular weight ranges. Extensive study of the technique has led to continuing improvement and expansion of applications. With careful control, the technique may be used as a quantitative as well as qualitative technique to determine molecular weight, charge, and concentration of each component. Numerous books and thousands of technical publications have appeared on the subject, notably, *Disc Electrophoresis and Related Techniques of Polyacrylamide Electrophoresis* by H. R. Maurer (Walter de Gruyter, New York, 1971), and *Laboratory Techniques in Biochemistry and Molecular Biology*, Vol. 1, Part 1, "Electrophoresis of Proteins in Polyacrylamide and Starch Gels" by A. H. Gordon (T. S. Work and E. Work, Ed., North Holland Publishing Company, Amsterdam-London, 1969). A commercially published bibliography documents many of the published papers in this field. *Disc Electrophoresis Base Bibliography* (1969-1973, Canalco, Inc., Rockville, Maryland. A leading journal, Journal of Chromatography (Elsevier Publishing Company, Amsterdam) publishes a monthly bibliography section which is divided into two main sections: A) Column Chromatography and B) Electrophoresis. Many of the listings (158 entries in the January 1974 issue) pertain to electrophoresis in polyacrylamide gels. Although the technique is highly successful and widely used, it remains difficult to execute. Several major difficulties can be identified:

1. A Lack of Reproducibility Between Individual Gels.

Each gel is prepared by a chemical polymerization of appropriate monomers. The sensitivity of the reaction to many possible components and impurities hinders reproducibility. Oxygen inhibition, reagent purity and initiator/catalyst levels are variables which have been studied. (A. Chrambach and D. Rodbard, *Separation Science*, 7, 663 (1972); Y. Pegon and C. Quincy, *Journal of Chromatography* 100,11 and 19 (1974); U. E. Loening D. H. L. Bishop, J. R. Claybrook, and S. Spiegelman, *Journal of Molecular Biology*, 26, 373 (1967)).

2. The Short Shelf Life of the Gels.

Crosslinked polyacrylamide materials are, like any amide, subject to hydrolysis to carboxyl groups. Such hydrolysis changes the polymer and introduces undesirable fixed charge into the gel. Since gels are most often run at a pH quite removed from neutrality, hydrolysis limits shelf life. (J. K. Inman and H. M. Dintzis, *Biochemistry* 8, 4074 (1969))

3. A Lack of Buffer Flexibility.

As commonly performed, the gel is polymerized in the buffer to be utilized. To run a sample at two different pH's, two polymerizations must be carried out and must be assumed to proceed with identical efficiency. If the buffer components affect the polymerization reactions, pH is no longer the only variable.

4. Skill in Preparation of Gels.

Substantial time and effort of a skilled operator are required in the preparation of polyacrylamide gels.

This invention pertains to a novel method of gel preparation for use in buffers that substantially remove the above limitations. To describe this invention, it is first necessary to divide the current technique (prior art) of polyacrylamide gel electrophoresis into three phases, or main steps. These steps are now described:

First Main Step

The first main step is the preparation of the gel. This is accomplished by preparing a solution of acrylamide, methylenebis-acrylamide or other crosslinking reagents in the buffer of choice. Catalyst (commonly N, N, N', N', - tetramethylethylenediamine) and initiator (ammonium persulfate) are then added. The solution is quickly transferred to the electrophoresis chamber (glass tubes or a rectangular area defined by glass plates are most commonly used), where polymerization takes place. The polymerization transfers the solution into a firm gel, typically within 1 hour.

Second Main Step

The second main step consists of placing the chamber containing polymerized gel in the electrophoresis cell where opposite ends of the chamber make immersion contact with two separate buffer reservoirs. In continuous electrophoresis, buffer solution of ionic strength, composition and pH identical to that incorporated into the gel during polymerization is added to each reservoir. In discontinuous electrophoresis a different buffer solution, but generally having a counter ion common with the buffer polymerized in the gel, is added to one of the reservoirs. Electrodes in each reservoir are connected to a direct current power supply. At this point a complete electric circuit exists and the apparatus is ready for application of a sample to be separated. Some operators, prior to applying the sample, apply potential to the circuit by means of the power supply. This is done to cause migration of residual ammonium persulfate and other charged residues of the gel formation process away from the sample application region of the gel. (J. Petropakis, A. F. Anglemier, and M. W. Montgomery, *Anal. Biochem.* 46, 594 (1972). This operation is termed "pre-electrophoresis".

Third Main Step

The third main step is the application of sample, establishment of appropriate voltage and current by means of the direct current power supply for a sufficient time to complete the resolution of components in the sample, and the identification, quantification, or isolation of the resolved zones.

This invention is primarily concerned with main step one and main step two. In this invention the individual events within these main steps are rearranged in such a manner that the first step, polymerization, is carried out under relatively optimum conditions in the absence of the buffer components ultimately to be used for electrophoresis with the gel formed. Instead of an electrophoretically useful buffer, an appropriate neutral salt solution of carefully chosen concentration is added to the solution of monomers, initiator, and catalyst. After completion of polymerization, as will be shown in examples below, a gel of useful properties is obtained that substantially removes the limitations of current practice listed above. The gels are then used in the second main step as defined above with the following change:

The buffer required for electrophoresis is placed in the electrophoresis cell reservoirs and DC voltage applied to the circuit prior to applying any sample for separation. This step is similar in mechanical aspect to the brief "pre-electrophoresis" described above as sometimes practiced in the prior art. In this invention, however, this step is continued until the neutral salt cast into the gel in main step one has migrated entirely out of the gel and into the reservoirs. As the ions of this salt leave the gel, ions of the buffer from the reservoirs enter the gel to replace them. When complete exchange has occurred, the gel is ready for main step three. This electrophoretic buffer introduction step can thus be utilized to introduce a variety of different buffers into a single type of gel. Further, the final state of the gel can be accurately predicted. Thus this procedure eliminates the lack of buffer flexibility and removes any effects upon the polymerization reaction of the buffer components.

The invention contemplates the use of any gel suitable for use in gel electrophoresis. In the preferred embodiment, a polyacrylamide gel is employed which is formed by an acrylamide cross-linked with a suitable cross-linking agent such as methylene bis-acrylamide. Any other suitable water soluble cross-linking agent may be utilized such as N, N' - diallyltartardiamide or ethylene diacrylate. The proportions are conventional. In a typical case, the total monomer content such as acrylamide and methylene bis-acrylamide will constitute 2–20% of the aqueous medium (2–20 grams of monomer/100 ml). Within the monomer components, the cross-linking agent constitutes about 1–10% by weight of the total monomer content.

The novel aspect of the invention is to include within the reaction medium a strong neutral salt having substantially no buffering capacity so that the reaction medium is at a neutral pH of 6–8 and preferably about 7. A concentration of the neutral salt is selected so as to ultimately provide the desired conductivity in the gel after the neutral salt has been replaced by the buffer forming species.

In general, an effective conductivity in the buffer-containing gel of about 200–20,000 micro mhos is desired. A neutral salt concentration of about 0.005N–1.0N and preferably about 0.01N–0.8N is selected to achieve this ultimate conductivity.

The buffer components introduced electrophoretically into the gel in exchange for the neutral salts are exchanged in equal ionic concentrations for the ions of corresponding charge in the gel. For example, the concentration of buffer forming cations electrophoretically introduced will precisely equal the concentration of salt cations eluted. Where the buffer-forming ions are a mixture, which may include strong ions, the total ionic concentration of the mixture exchanged will equal the concentration of strong salts eluted, with the relative proportions of the various buffer forming ions introduced into the gel equal to that at the outset (subject to changes due to differences in ion mobility, which are not significant in most cases).

In general, where the starting buffer solution to be introduced includes relatively highly ionized forms of ions which will produce a relatively high conductivity in the gel, a lower neutral salt concentration in the gel will be utilized to achieve a conductivity within the desired range above stated. The converse is true when utilizing relatively slightly ionized buffer forming ions.

As noted, the buffering ions to be introduced may include strong ions. However, the total mixture of buffering ions to be introduced must provide a buffering function in the gel and thus the ions to be introduced must include at least one cation having a titratable $pK_a$ between 2 and 10 and at least one anion having a titratable $pK_a$ between 2 and 10. The difference between the latter two $pK_a$'s should not be greater than 5 and preferably should not be greater than 3.

The choice and selection of buffer solutions to be introduced and which will meet the conductivity requirements and buffering requirements in the gel is broad. The working examples given below illustrate one suitable system. The following table illustrates a series of alternative buffers for electrophoretic introduction. In the table the "Operating pH" is the pH which results after the buffers are exchanged in the gel. Many other buffer systems can be used to achieve the broad purposes of this invention. In some cases, especially where the buffer solution to be introduced contains strong ions, a trial and error technique may be needed to determine suitability of the system. The selected buffers can be introduced into the gel and the performance of the gel measured. Alternatively, a solution can be made up containing the ionic species that will be found in the gel after the exchange and separately measured to determine if the buffering capacity and conductivity is suitable for the separation to be performed.

| Operating pH | Acid | $pK_a$ | Base | $pK_a$ |
|---|---|---|---|---|
| 9.5 | Cyclohexylaminopropane sulfonic acid "CAPS" | 10.4 | 2-amino-2-methyl-1,3-propanediol | 8.67 |
| 8.9 | Glycine | 9.6 | Tris | 8.1 |
| 8.5 | Boric acid | 9.23 | Triethanolamine | 7.8 |
| 7.8 | N,N-bis[2-hydroxyethyl] glycine "Bicine" | 8.35 | Imidazole | 6.95 |
| 7.5 | Bicine | 8.35 | 2,6-lutidine | 6.77 |
| 7.0 | Morpholinopropane sulfonic acid "MOPS" | 7.15 | 2,6-lutidine | 6.77 |

-continued

| Operating pH | Acid | pK$_a$ | Base | pK$_a$ |
|---|---|---|---|---|
| 6.0 | MOPS 2[N-morpholino]ethane | 7.15 | 3-hydroxypyridine | 4.86 |
| 5.5 | sulfonic acid "MES" or Cacodylic acid | 6.15 | 3-hydroxypyridine | 4.86 |
| 5.2 | MES or Cacodylic acid | 6.15 | 4-aminobutyric acid | 4.23 |
| 4.5 | Propionic acid | 4.87 | 4-aminobutyric acid | 4.23 |
| 4.0 | Acetic acid | 4.73 | Glycylglycine | 3.15 |
| 3.6 | Acetic acid | 4.73 | Glycine | 2.45 |
| 2.7 | Citric acid | 3.1 | Glycine | 2.45 |

In the practice of the present invention it is important to determine when the exchange of the buffer for the neutral salt is complete. If the exchange is discontinued before there is a complete replacement of the neutral salts by the buffer ions, the utility of the gel for electrophoresis will be impaired, as may be evidenced in buffer discontinuities which produce undesired sample "unstacking" phenomena detrimental to the separation. To this end the present method includes the use of a tracking dye placed at the top of a gel column or at one end of a slab. These tracking dyes comprise appropriately colored organic dyes in a suitable diluent. In the preferred embodiment, the tracking dye is made up in a sucrose solution and diluted with the buffer being introduced.

The following examples will illustrate the preferred embodiment:

EXAMPLE 1

An aqueous monomer solution was prepared which contained 7.312 grams of acrylamide, 0.1875 grams of methylene-bis-acrylamide, 1.245 grams ammonium sulfate, 0.006 grams TMEDA (N, N, N', N',-tetramethylethylenediamine) in a volume of ca. 75 cc. This solution was adjusted to a pH of 7.5 with 2N sodium hydroxide or 2N hydrochloric acid before transfer and final dilution to a 100 ml volumetric flask, to exactly 100 ml.

The solution was placed in a vacuum chamber (bell jar, vacuum oven, etc.) and evacuated to 28 in. of Hg for 15 min. The vacuum was released and 0.15 ml of an 8% (W/V) aqueous solution of ammonium persulfate solution was added. The solution was volumetrically dispensed into glass tubes (5.5mm ID, 7.0 mm OD, 125 mm length). The ends of the tubes had been sealed with Parafilm$^{TM}$ plastic film and were supported in a vertical position in a plastic strand. A volume of 2.5 ml was added to each tube. Individual tubes containing monomer solution were carefully overlayered with 100 ul per tube of a solution containing 1.245 grams of ammonium sulfate in 100 ml of water. The tubes were allowed to set, unperturbed, for 18 hours. At the end of this period, the tubes contained a polymerized gel of ca. 100 mm length. The gels were rinsed with deionized water and placed in a commercial electrophoresis cell (Bio-Rad Model 150 Electrophoresis Cell). Both reservoirs were filled with a buffer containing 22.8 gm/liter of Tris (2-amino-2(hydroxymethyl)-1,3 propane diol) and 14.15 gm/liter of glycine (aminoacetic acid), pH 8.9. A tracking dye solution was prepared by adding diluted buffer (1 volume) with water (4 volumes). Seven ml of diluted buffer was added to 3 grams of sucrose. A weight of 0.04 grams of Bromophenol Blue was dissolved in this solution. This dense solution could be layered through the electrophoresis buffer onto the gel surface as a compact layer. A volume of 10 ul was layered onto each gel to provide a visible indicator of the electrophoretic buffer introduction. A voltage of 100V (DC anode in the lower buffer chamber) was applied to the cell. The current drawn was initially ca. 8ma./gel. The voltage was maintained at 100V until the Bromophenol Blue dye had completely traversed the length of the gel. The current observed at this point was ca. $^{1.0}$ ma/gel.

A gel treated in such a manner was removed from the glass tube and soaked (eluted) in 10 cc of distilled water. The measured pH of the solution, after 24 hours, was pH 8.9. This was taken as the operating pH of the gel. A similar gel was cut into four equal segments. Elution of each segment produced solutions of identical pH of 8.9.

A sample of normal human serum was run on a gel equilibrated with this tris/glycine buffer. Upon staining and destaining, as commonly practiced, a pattern of sharply separated bands was observed. The pattern obtained was virtually identical to that obtained by prior techniques (B. J. Davis, Ann. New York Acad. Sci. 121, 404 (1964); S. Hjerten, S. Jerstedt and A. Tiselius, Anal. Biochem. 11, 219 (1965)).

EXAMPLE 2

Gels were prepared from a monomer solution identical to that described in Example 1. The polymerization was carried out in a commercially available apparatus for gel tube casting. This apparatus (Bio-Rad Laboratories Model 210 Precision Gel Preparation System) was used according to the manufacturer's instructions. One of the gels formed in this manner was placed into a cell containing a buffer made of glycine (14.15gm/liter) and acetic acid (12.3 g/liter), pH 3.6. A tracking dye solution (0.4% methyl green in a 4:1 dilution of the buffer containing 30% sucrose) was applied and the electrophoretic buffer introduction carried out at 100V (DC constant voltage, cathode in the lower chamber). When the tracking dye had eluted, the gels were ready for sample application. A sample of a commercial preparation of calf thymus histones (10mg/ml) was diluted with tracking dye and applied to a gel (10 ul of 2:1:1:: protein:tracking dye:distilled water). This sample was run at 100V (DC, cathode in the lower chamber) for 15 minutes, then at 200V DC until the tracking dye had just reached the bottom of the gel.

Staining and destaining produced a pattern of ca. 5 main bands which were judged well defined and well resolved. (G. R. Shepherd and L. R. Gurley, Anal. Biochem. 14, 356 (1966); G. R. Shepherd, Anal. Biochem. 14, 364 (1966); Bio-Rad Laboratories, Product Information Bulletin 2009, April 1974).

EXAMPLE 3

A gel was prepared from a monomer solution containing 1.245 gm $(NH_4)_2SO_4$, 9.75 gm acrylamide, 0.250 gm methylene-bis-acrylamide and .0006 gm of TMEDA. After vacuum degassing 0.15 ml of 8% ammonium persulfate was added. The gels were polymerized as in Example 2. The polymerized gels had the acetic acid/glycine buffer introduced electrophoretically as in Example 2. A gel was removed from the tube and eluted with deionized water and the pH measured. The pH was 3.6.

EXAMPLE 4

A gel prepared as in Example 2 (7.5% total monomer) was removed from the tube and the optical density was measured utilizing a Beckman DU monochromator equipped with a Gilford Instrument Laboratories' detection system and gel scanning accessory. The instrument was zeroed using distilled water. The measured OD of this gel was 0.14 at 260 nm. A gel from Example 3 (10% total monomer) had an OD at 260 nm of 0.10. A solution of 0.0005 gm of acrylamide per ml of $H_2O$ gave an OD at 260 nanometers of 0.335 when measured in the quartz "boat" used to contain the gel. Since the monomer solutions in Examples 2 and 3 contained 0.075 and 0.10 gm of acrylamide per ml of solution, respectively, it was concluded that the gels contained considerably less than 1% unreacted monomer (0.00075 gm/ml and 0.001 gm/ml - 1% of original monomer for a 7.5 and 10% total monomer gel). For comparison, a commercially prepared gel (7.5% total monomer) exhibited an $OD_{260}$ of 1.4. This gel was apparently cast in the presence of an operating buffer and no electrophoretic buffer introduction was recommended.

While examples have used ammonium sulfate as the neutral salt, other strongly ionized neutral salt could be substituted. Typical examples are ammonium acetate, sodium sulfate, sodium chloride, potassium sulfate, potassium acetate, and potassium chloride.

We claim:

1. A pre-cast crosslinked polyacrylamide adapted for use in gel electrophoresis and containing therein a strongly ionizable neutral salt in a concentration of about 0.005N – 1.0N the pH of said polyacrylamide being between about 6 and 8.

2. A pre-cast crosslinked polyacrylamide in accordance with claim 1 wherein said neutral salt is present in a concentration of about 0.01N – 0.8N.

3. A pre-cast crosslinked polyacrylamide in accordance with claim 1 wherein said neutral salt is ammonium sulfate.

4. A pre-cast crosslinked polyacrylamide in accordance with claim 1 wherein the acrylamide crosslinking agent is methylene bis-acrylamide.

5. A pre-cast crosslinked polyacrylamide in accordance with claim 1 wherein the total concentration of monomer in the solution forming said polyacrylamide is about 2–20% and the proportion of crosslinking agent relative to total monomer content is about 1–10%.

6. A pre-cast crosslinked polyacrylamide in accordance with claim 1 wherein the pH in said polyacrylamide is about 7.

7. An improved method for gel electrophoresis comprising: providing a gel suitable for electrophoresis and containing a strong neutral salt at a pH of about 6–8, electrophoretically exchanging a buffer for said strong salt, and applying a sample for resolution into its components to said buffer-containing gel.

8. The improved method in accordance with claim 7 and including applying a tracking dye to said gel to indicate the completion of exchange of buffer for said salt.

9. The improved method in accordance with claim 7 wherein said buffer contains at least one cation having a titratable $pK_a$ of 2–10 and at least one anion having a titratable $pK_a$ of 2–10, wherein the difference between said $pK_a$'s is not more than 5.

10. The improved method in accordance with claim 9 wherein the difference between said $pK_a$'s is not more than 3.

11. The improved method in accordance with claim 9 wherein said buffer also contains strong ions.

12. The improved method in accordance with claim 7 wherein the concentration of said strong neutral salt and the components of said buffer are initially selected to provide an effective conductivity in said buffer-containing gel of about 200–20,000 micro mhos.

13. The improved method in accordance with claim 7 wherein said gel is provided by polymerizing acrylamide and a crosslinking agent in an aqueous media containing said strong neutral salt at a pH of about 6–8.

14. In the method for resolving components of a sample by gel electrophoresis in a polyacrylamide gel containing a buffer, the improvement comprising preforming said gel in the absence of a buffer and in the presence of a strong neutral salt to incorporate the salt in the gel, and thereafter electrophoretically introducing a buffer into said gel in exchange for said neutral salt prior to the application of the sample to said gel.

* * * * *